US 6,652,879 B2

(12) United States Patent
Opheim

(10) Patent No.: US 6,652,879 B2
(45) Date of Patent: *Nov. 25, 2003

(54) FLAVORED GELATIN CAPSULE AND METHOD OF MANUFACTURE

(76) Inventor: Joar Opheim, 117 Sea Ter. Way, Aptos, CA (US) 95003

(*) Notice: Subject to any disclaimer, the term of this patent is extended or adjusted under 35 U.S.C. 154(b) by 0 days.

This patent is subject to a terminal disclaimer.

(21) Appl. No.: 10/041,877

(22) Filed: Oct. 22, 2001

(65) Prior Publication Data

US 2002/0058064 A1 May 16, 2002

Related U.S. Application Data

(63) Continuation of application No. 09/416,017, filed on Oct. 6, 1999, now Pat. No. 6,346,231.

(51) Int. Cl.$^7$ .............................. A61K 9/48; A61K 35/66
(52) U.S. Cl. ...................... 424/451; 424/455; 424/456; 424/523
(58) Field of Search ................................ 424/451, 455, 424/456, 523

(56) References Cited

U.S. PATENT DOCUMENTS

| | | | | |
|---|---|---|---|---|
| 5,141,961 A | * | 8/1992 | Coapman | 514/289 |
| 5,656,667 A | | 8/1997 | Breivik | |
| 5,874,418 A | * | 2/1999 | Stella et al. | 514/58 |
| 5,955,102 A | | 9/1999 | Gorenbein | |
| 6,346,231 B1 | * | 2/2002 | Opheim | 424/45 |

* cited by examiner

Primary Examiner—Thurman K. Page
Assistant Examiner—Isis Ghali
(74) Attorney, Agent, or Firm—Howard E. Lebowitz

(57) ABSTRACT

A flavored gelatin capsule and the method of manufacture of the flavored capsule is provided. The capsule may comprise (a) from about 10 to about 70 parts by weight of gelatin; (b) from about 10 to about 35 parts by weight of a suitable polyol, such as glycerol; (c) from about 8 parts by weight of water; and (c) various parts by weight of particular water soluble flavorings. The contents of the capsule may also be flavored. The composition is particularly useful in improving the palatability of fish oil medicinals.

6 Claims, 2 Drawing Sheets

FLAVORED GELATIN CAPSULE AND METHOD OF MANUFACTURE

This application is a continuation of my application Ser. No. 09/416,017 filed on Oct. 6, 1999 now U.S. Pat. No. 6,346,231, and the entire disclosure thereof is hereby incorporated herein by reference.

BACKGROUND OF THE INVENTION

1. Field of the Invention

This invention relates to capsule formulations, medicinal and nutritive dose encapsulations and methods of manufacture of capsules. More specifically, the invention introduces flavoring into the manufacture of capsules and encapsulated doses.

2. Conventional Art

The taste of many medicinal and nutritive components can be quite distinctive and potentially unpleasant. Improvements in the taste of certain drugs and nutritional supplements can lead to a higher compliance by consumers. A higher compliance will result in greater commercial success for the drug and supplement manufacture and in increased health and well being particular consumers.

Taste is both a matter of purely subjective preference. Yet human taste is also strongly influenced by experience and cultural impressions. Broad generalizations about consumer taste presence can thus sometimes be relied upon in predicting market acceptance of specific drug and nutritive formulations. In Norway, for example the tastes of fish oils are far more palatable than in the United States. As a consequence of this United States market aversion to the taste of fish oils, many residents of the United States are less willing to ingest fish oils and will therefore not benefit from the nutritional and medicinal qualities of fish oils.

Yet the composition of certain fish oils includes elements that are identified in medical literature as providing significant health benefits. Polyunsaturated fatty acids, to include long chain Omega 3 fatty acids such as eicosapentenoic acid (EPA) and docosahexenoic acid (DHA) are present in the livers of lean fish and other tissues of fatty fish. The human body cannot synthesize these fatty acids nor can it derive them from other fatty acids. As these fatty acids provide both medicinal and nutritional benefits, an intake of up two grams per day has been recommended by certain medical authorities.

It is suspected that Eicosanoids derived from EPA might have an anti-inflammatory effect on humans. It has been suggested that EPA might decrease blood levels of TG lipids, increase blood levels of high density lipids (HDL), decrease blood clotting, reduce the incidence of cardiac arrhythmia and stabilize heart rhythm.

It has been suggested that DHA may also decrease blood levels of TG lipids, increases blood levels of high density lipids (HDL). Furthermore, DHA might lower blood pressure, attack early phases of inflammation, facilitate the growth, development and function of the central nervous system and improves the clinical symptoms of depression and schizophrenia.

Increasing the consumption of recommended doses of certain Omega-3 fatty acids might therefore have a medically and nutritionally beneficial affect on many consumers and patients. Yet conventional techniques to improve the palatability of fish oils and other subjectively harsh tasting substances are limited in the prior art to the addition of flavorings into a mixture of the substances themselves. The flavoring of capsules of encapsulated formulations has been absent in the conventional art.

OBJECTS OF THE INVENTION

It is therefore an object of the present invention to provide a method of manufacture of gelatin capsules.

It is another object of the present invention to provide a gelatin capsule comprising a flavor.

It is an additional object of the present invention to optionally provide a flavored gelatin capsule containing a fish oil.

It is an yet another object of the present invention to optionally provide a flavored gelatin capsule containing a flavored fish oil.

SUMMARY OF THE INVENTION

These and other objects and advantages of the present invention are achieved by providing a flavored gelatin capsule comprising a water soluble flavor. The flavored gelatin capsule may include about 10 to about 70 parts by weight of a gelatin, about 10 to about 35 parts by weight of a glycerol, about 8 to about 35 parts by weight of a moisturizer and about 1 parts by weight of the water soluble flavoring. The flavoring of the capsule improves the taste and palatability of the capsule and will subjectively improve the taste of the gelatin and a dose or contents contained within the flavored gelatin capsule to individual consumers or patients.

The flavor may be one of, or a combination of suitable flavors known in the art, to include berry, strawberry, chocolate, cocoa, vanilla, lemon, nut, almond, cashew, macadamia nut, coconut, blueberry, blackberry, raspberry, peach, lemon, lime, mint, peppermint, orange, banana, chili pepper, pepper, cinnamon, and pineapple.

The gelatin capsule composition may include a polyol, such as sorbitol, glycerol or other suitable softening agent known in the art.

A preferred embodiment of the present invention includes flavoring the contents of the gelatin capsule in addition to flavoring the gelatin capsule. In particular, an oil soluble flavoring may be optionally mixed with a fish oil that is encapsulated within the capsule. The oil soluble flavoring may be similar to the taste of the flavor of the capsule, e.g., strawberry and strawberry, or the taste of the oil flavoring may be complementary to the capsule flavoring, e.g., banana and strawberry.

Fish oil containing Omega 3 fatty acids such as eicosapentenoic acid (EPA) and docosahexenoic acid (DHA) are one appropriate subject of inclusion into certain preferred embodiments of the present invention. The capsule of these certain preferred embodiments is flavored and the fish oil may optionally be flavored.

The method of the present invention includes the manufacturing process steps of combining gelatin, a glycerol or a polyol like sorbitol as a softener, water or a moisturizer containing water, a flavoring agent and optionally a coloring agent such as a titanium oxide, keratin or other suitable coloring agent known in the art.

Modified vegetable starch is substituted for gelatin in certain preferred embodiments of the present invention. Where gelatin is used, the gelatin may be a suitable mammalian or fish gelatin known in the art. The suitable gelatin or vegetable starch selected is used as a principal forming agent of the capsule.

DETAILED DESCRIPTION OF THE PREFERRED EMBODIMENTS

In describing the preferred embodiments, certain terminology will be utilized for the sake of clarity. Such terminology is intended to encompass the recited embodiment, as well as all technical equivalents which operate in a similar manner for a similar purpose to achieve a similar result.

Figure 1:
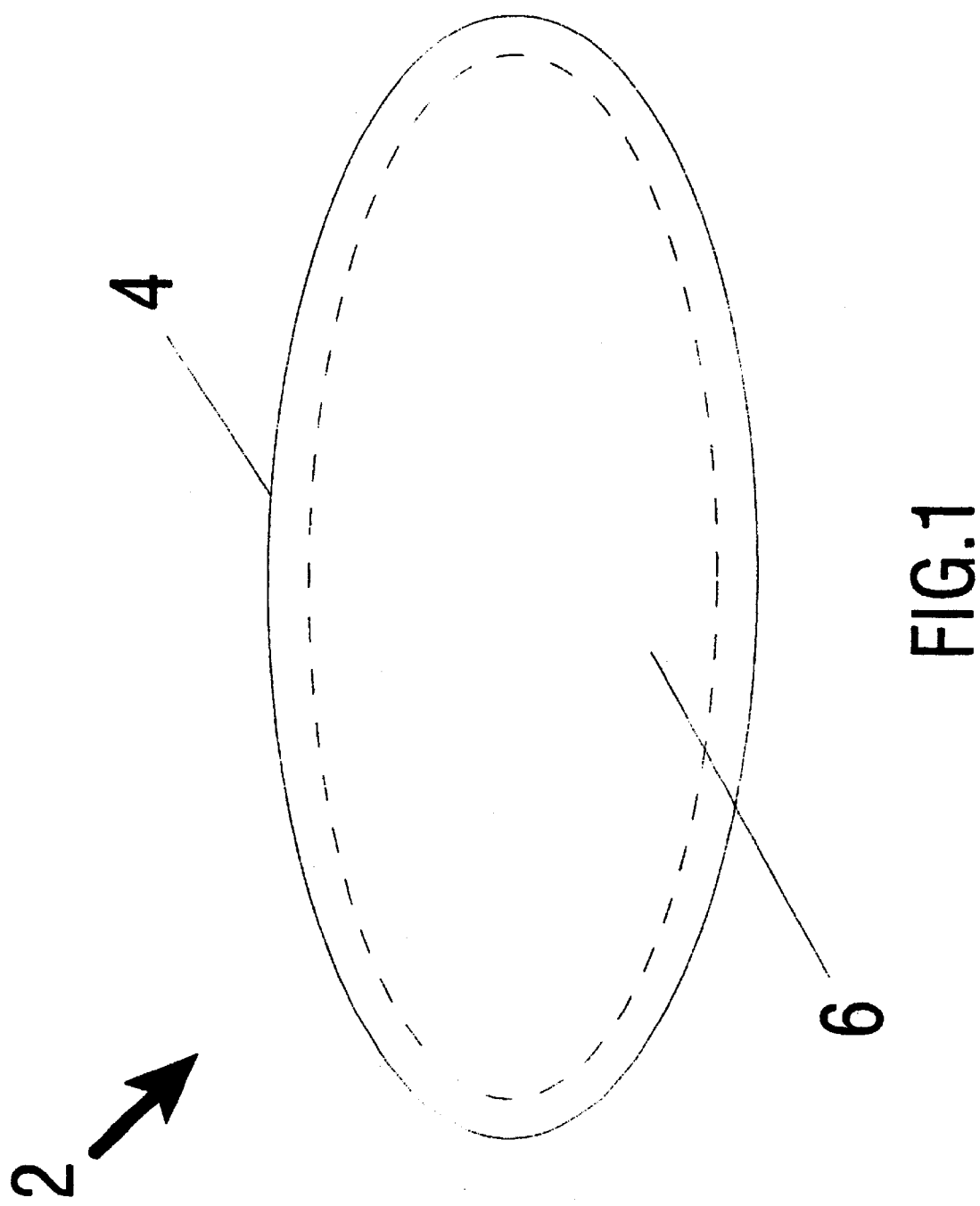
FIG. 1 is a flavored gelatin capsule containing a fish oil dose.

Referring now to FIG. 1, an encapsulated composition of a gelatin capsule and fish oil 2, or fish oil capsule 2, is formed by the encapsulation of a dose of fish oil 6 by a gelatin capsule 4. The gelatin capsule 4 is made of gelatin, glycerol, water, a flavoring and optionally a coloring agent. The fish oil dose 6 includes 180 mg of EPA and 120 mg of DHA.

Figure 2:
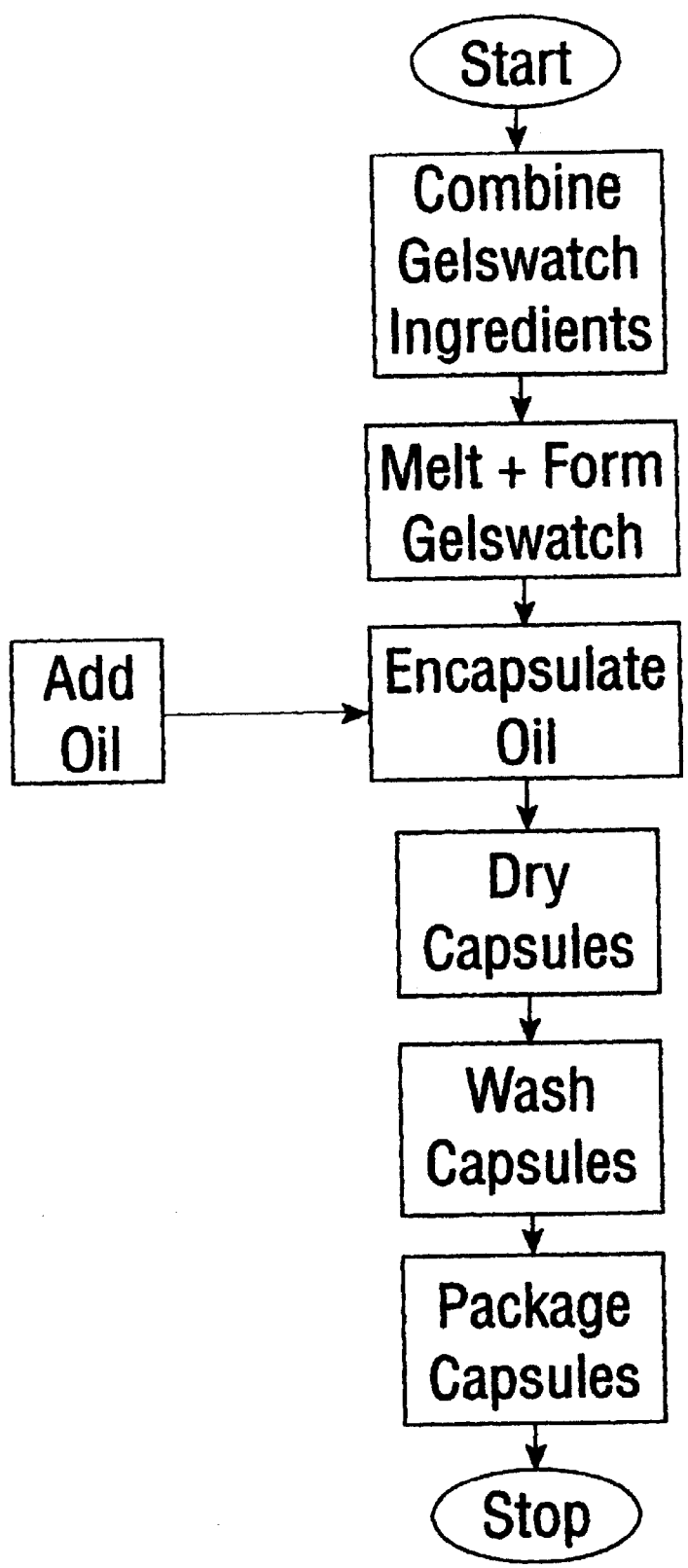
FIG. 2 is manufacturing process flow chart illustrating an embodiment of the method of the present invention.

Referring now to FIGS. 1 and 2, the manufacturing process of the preferred embodiment 2 of includes the steps of combining gelswatch ingredients, melting and forming a liquefied gelswatch, delivering the liquefied gelswatch and the fish oil 6 to an encapsulation machine, encapsulating a dose of fish oil, drying the encapsulated dose, washing the encapsulated dose and packaging the fish oil capsules 2 for shipment.

The gelswatch ingredients may include gelatin or a gelatin substitute such as modified starch or other suitable gelatin substitute known in the art, a softener such as glycerol or sorbitol or other suitable polyol or other gelatin softener known in the art, a flavoring agent such as strawberry flavor Firmenich #52311A or other suitable gelatin capsule flavoring known in the art and optionally a coloring agent such as keratin or other suitable gelatin capsule coloring agent known in the art.

The preferred embodiment 2 may be formed from a gelswatch mixture of 45 parts by weight of gelatin, 20 parts by weight of glycerol, 35 parts by weight of water and 0.5 or more parts by weight of strawberry flavor Firmenich #52311A. The gelswatch ingredients are then heated to about 60 degrees to 70 degrees Celsius and mixed together. The capsule is made of the gelswatch material. The liquefied gelswatch and the fish oil 6 is then poured into an encapsulation machine. The encapsulation machine then forms the fish oil capsule 2 comprising the fish oil dose 6 encapsulated by the gelatin capsule 4.

In certain alternate preferred embodiments of the present invention the range of water parts initially combined with the gelswatch may range from about 10 parts by weight to about 45 parts by weight; the amount of gelatin initially combined into the gelswatch may range from 10 parts by weight to about 70 parts by weight; and the amount of glycerol or other suitable softener known in the art may range from about 10 parts by weight to about 35 parts by weight.

The capsule composition 2 comprises about 500 milligrams of the fish oil dose 6 and about 240 milligrams of capsule 4 as formed from the gelswatch.

The fish oil capsule composition 2 is then dried at a temperature of about 20 degrees Celsius. The water content of the gelatin capsule is reduced to about 8%+/−2% by evaporation during the drying process step. The capsule 2 is then washed and packaged for shipment.

Experimental testing of the effects of varying amounts of the flavoring in both the capsule 4 and the fish oil 6 has shown that a concentration of 0.5% in the fish oil 6 of the Firmenlch #52311A flavor will degrade in less than a year's span to below a desirable level of potency to the average North American consumer. Levels of 1 part by weight are preferred in order to extend the effective shelf life of the composition 2 beyond one year.

In addition, stream of commerce testing of concentration levels of Firmenich #52311A has shown that a level in excess of about 1.0 part by weight of the Firmenich #52311A in the capsule 4 provides an unexpected increase in the palatability of the composition 2 by generating a flavored bouquet from the capsules 2, whereby the consumer is greatly encouraged to ingest the composition 4 in a favorable response to his or her olfactory appreciation of the bouquet.

Certain preferred embodiments comprise fish oil presenting concentrations of Omega 3 fish as high or higher than 80% of the total weight of the dose 6, wherein the fish oil may include 50% DHA of the total weight of the dose 6, 20% EPA of the total weight of the dose 6 and about 10% by weight of other Omega 3 compounds. The concentration levels of the flavoring additive of a fish oil dose may, in certain preferred embodiments of the present invention having about 80% by weight of Omega 3 components, is reduced to from about 0.25% by weight to about 0.50% by weight of the dose 6

Those skilled in the art will appreciate that various adaptations and modifications of the just-described preferred embodiments can be configured without departing from the scope and spirit of the invention. Therefore, it is to be understood that, within the scope of the appended claims, the invention may be practiced other than as specifically described herein.

I claim:

1. A flavored gelatin capsule suitable for encapsulating a dose, said flavored gelatin capsule comprising gelatin, a gelatin softener, water, and a water soluble flavoring, wherein said water soluble flavoring is present in said flavored gelatin capsule in a concentration which is in the range between about 0.25% and about 1.5% of said flavored gelatin capsule, and wherein said water is present in said flavored gelatin capsule in a concentration in the range between about 6% and about 10% of said flavored gelatin capsule, whereby the palatability of a dose encapsulated in said flabored gelatin capsule is improved by the water soluble flavoring.

2. The flavored gelatin capsule of claim 1 further comprising a dose encapsulated therein.

3. The flavered gelatin capsule of claim 1 wherein the water soluble flavoring comprises a flavor chosen from the group consisting of berry, strawberry, chocolate, cocoa, lemon, but, almond, cashew, macadamia nut, coconut, blueberry, blackberry, raspberry, peach, lemon, lime, mint, orange, banana, chili pepper, pepper, cinnamon, and pineapple.

4. The flavored gelatin capsule of claim 1 wherein the gelatin sofener is present in a concentration in the range between 10% and 35% of said flavored gelatin capsule.

5. The flavored gelatin capsule of claim 2 wherein said dose comprises ingredients chosen from the group consisting of medicinal conponents and nutritive components.

6. THe flavored gelatin capsule fo claim 5 wherein the concentration of water-soluble flavoring present in said gelatin capsule is in the range between about 0.5% and about 1.5%.

* * * * *

(12) EX PARTE REEXAMINATION CERTIFICATE (8216th)
United States Patent
Opheim

(10) Number: US 6,652,879 C1
(45) Certificate Issued: May 10, 2011

(54) FLAVORED GELATIN CAPSULE AND METHOD OF MANUFACTURE

(75) Inventor: Joar Opheim, Aptos, CA (US)

(73) Assignee: Union Bank of California, N.A., San Francisco, CA (US)

Reexamination Request:
No. 90/010,734, Feb. 3, 2010

Reexamination Certificate for:
Patent No.: 6,652,879
Issued: Nov. 25, 2003
Appl. No.: 10/041,877
Filed: Oct. 22, 2001

Related U.S. Application Data

(63) Continuation of application No. 09/416,017, filed on Oct. 6, 1999, now Pat. No. 6,346,231.

(51) Int. Cl.
*A61K 9/48* (2006.01)
*A61K 9/64* (2006.01)
*A61K 9/66* (2006.01)
*A61K 35/56* (2006.01)
*A61K 35/60* (2006.01)
*A61K 47/46* (2006.01)

(52) U.S. Cl. .................. 424/451; 424/455; 424/456; 424/523

(58) Field of Classification Search .................. 424/45
See application file for complete search history.

(56) References Cited

U.S. PATENT DOCUMENTS 4,428,927 A * 1/1984 Ebert et al. .................. 424/440
4,780,316 A * 10/1988 Brox .......................... 424/456

OTHER PUBLICATIONS

Stanley, J.P., "Soft Gelatin Capsules" in The Theory and Practice of Industrial Pharmacy, Leon Lachman, Herbert A. Lieberman & Joseph L. Kanig, eds. pp. 398–412, 1986.*
Banner Gelatin Products Corporation, Product Labels, 1977.*
Scherer Corporation, Sales of Flavored Fish Oil Capsules Product Labels, 1974–1976.*

* cited by examiner

*Primary Examiner* — Gary L. Kunz

(57) ABSTRACT

A flavored gelatin capsule and the method of manufacture of the flavored capsule is provided. The capsule may comprise (a) from about 10 to about 70 parts by weight of gelatin; (b) from about 10 to about 35 parts by weight of a suitable polyol, such as glycerol; (c) from about 8 parts by weight of water; and (c) various parts by weight of particular water soluble flavorings. The contents of the capsule may also be flavored. The composition is particularly useful in improving the palatability of fish oil medicinals.

US 6,652,879 C1

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2, 3, 5 and 6 are cancelled.

Claims 1 and 4 are determined to be patentable as amended.

New claims 7-16 are added and determined to be patentable.

1. *A flavored fish oil capsule comprising:*
a) a flavored gelatin capsule suitable for encapsulating a dose, said flavored gelatin capsule comprising gelatin, a gelatin softener, water, and a water soluble flavoring, wherein said water soluble flavoring is present in said flavored gelatin capsule in a concentration which is in the range between about 0.25% and about 1.5% of said flavored gelatin capsule, and wherein said water is present in said flavored gelatin capsule in a concentration in the range between about 6% and about 10% of said flavored gelatin capsule, whereby the palatability of a dose encapsulated in said [flabored] *flavored* gelatin capsule is improved by the water soluble flavoring, *and wherein the water soluble flavoring comprises a flavor chosen from the group consisting of berry, strawberry, chocolate, cocoa, lemon, nut, almond, cashew, macadamia nut, coconut, blueberry, blackberry, raspberry, peach, lemon, lime, mint, orange, banana, chili pepper, pepper, cinnamon, and pineapple; and* b) *a fish oil dose, said flavored gelatin capsule encapsulating said fish oil dose.*

4. The flavored [gelatin] *fish oil* capsule of claim 1 wherein the gelatin [sofener] *softener* is present in a concentration in the range between 10% and 35% of said flavored gelatin capsule.

*7. The flavored fish oil capsule of claim 1, wherein the fish oil dose comprises one or more Omega 3 fatty acids.*

*8. The flavored fish oil capsule of claim 7, wherein at least 80% of the total weight of the fish oil dose comprises Omega 3 fatty acids.*

*9. The flavored fish oil capsule of claim 7, wherein the fish oil dose comprises at least one of the Omega 3 fatty acids selected from the group consisting of eicosapentanoic acid and docosahexanoic acid.*

*10. The flavored fish oil capsule of claim 9, wherein the fish oil dose comprises eicosapentanoic acid and docosahexanoic acid.*

*11. The flavored fish oil capsule of claim 10, wherein the eicosapentanoic acid comprises about 20% of the total weight of the fish oil dose and the docosahexanoic acid comprises about 50% of the total weight of the fish oil dose.*

*12. The flavored fish oil capsule of claim 1, wherein the fish oil dose comprises an oil soluble flavoring.*

*13. The flavored fish oil capsule of claim 12, wherein the oil soluble flavoring comprises a flavor chosen from the group consisting of berry, strawberry, chocolate, cocoa, lemon, nut, almond, cashew, macadamia nut, coconut, blueberry, blackberry, raspberry, peach, lemon, lime, mint, orange, banana, chili pepper, pepper, cinnamon, and pineapple.*

*14. The flavored fish oil capsule of claim 12, wherein the oil soluble flavoring comprises the same flavor as the water soluble flavoring.*

*15. The flavored fish oil capsule of claim 12, wherein the oil soluble flavoring comprises a different flavor than the water soluble flavoring.*

*16. The flavored fish oil capsule of claim 12, wherein the oil soluble flavoring is present at a concentration of 0.5% of said fish oil dose.*

\* \* \* \* \*